United States Patent
Gotman et al.

(10) Patent No.: US 11,830,605 B2
(45) Date of Patent: Nov. 28, 2023

(54) IMAGE VISUALIZATION OF MEDICAL IMAGING STUDIES BETWEEN SEPARATE AND DISTINCT COMPUTING SYSTEM USING A TEMPLATE

(71) Applicant: KONINKLIJKE PHILIPS N.V., Eindhoven (NL)

(72) Inventors: Shlomo Gotman, Haifa (IL); Eran Rubens, Haifa (IL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 11 days.

(21) Appl. No.: 14/784,850

(22) PCT Filed: Apr. 23, 2014

(86) PCT No.: PCT/IB2014/060940
§ 371 (c)(1),
(2) Date: Oct. 15, 2015

(87) PCT Pub. No.: WO2014/174461
PCT Pub. Date: Oct. 30, 2014

(65) Prior Publication Data
US 2016/0062956 A1 Mar. 3, 2016

Related U.S. Application Data

(60) Provisional application No. 61/815,341, filed on Apr. 24, 2013.

(51) Int. Cl.
*G16H 30/40* (2018.01)
*G06F 40/106* (2020.01)
(Continued)

(52) U.S. Cl.
CPC ........... *G16H 30/40* (2018.01); *G06F 40/106* (2020.01); *G06F 40/186* (2020.01); *G16H 30/20* (2018.01)

(58) Field of Classification Search
CPC .... G06F 19/321; G06F 40/106; G06F 40/186; G16H 30/20
See application file for complete search history.

(56) References Cited

U.S. PATENT DOCUMENTS 5,182,656 A * 1/1993 Chevion .............. H04N 1/4115
358/450
5,191,525 A * 3/1993 LeBrun .................... B07C 3/00
715/229

(Continued)

FOREIGN PATENT DOCUMENTS

| CN | 1818974 A | 8/2006 |
|---|---|---|
| JP | 2007179192 A | 7/2007 |
| WO | 2011064695 A2 | 6/2011 |

OTHER PUBLICATIONS

"Digital Imaging and Communications in Medicine (DICOM), Part 3: Information Object Definitions" (1,439 pages), 2011 National Electrical Manufacturers Association. <https://dicom.nema.org/medical/dicom/2011/11_03pu.pdf> (Year: 2011).*

(Continued)

*Primary Examiner* — Kavita Stanley
*Assistant Examiner* — Tyler Schallhorn

(57) ABSTRACT

A system and/or method that facilitates sharing image viewing context between vendor visualization applications without integration of different software application from different vendors packages is describe herein. In one instance, a visualization computing system (102) includes a processor (116) that executes computer readable instructions that capture a visual context of an imaging study displayed via a basic visualization application running on a vendor computing system, identify the study based on the captured visual context, load the study on the visualization computing system, and launch an advanced visualization application, which allows viewing and manipulation of the loaded study (Continued)

using advanced visualization tools unavailable by the basic visualization application.

16 Claims, 6 Drawing Sheets

(51) Int. Cl.
*G06F 40/186* (2020.01)
*G16H 30/20* (2018.01)

(56) References Cited

U.S. PATENT DOCUMENTS

| | | | | |
|---|---|---|---|---|
| 5,235,510 | A * | 8/1993 | Yamada | G06F 19/321 600/300 |
| 5,241,472 | A | 8/1993 | Gur et al. | |
| 5,258,855 | A * | 11/1993 | Lech | G06K 9/2054 358/448 |
| 5,369,508 | A * | 11/1994 | Lech | G06K 9/2054 358/448 |
| 5,625,465 | A * | 4/1997 | Lech | G06K 9/2054 358/403 |
| 5,768,416 | A * | 6/1998 | Lech | G06K 9/2054 382/175 |
| 5,793,887 | A * | 8/1998 | Zlotnick | H04N 1/4115 382/151 |
| 6,886,136 | B1 * | 4/2005 | Zlotnick | G06K 9/00 358/462 |
| 7,424,679 | B1 | 9/2008 | Lamer et al. | |
| 7,489,810 | B2 * | 2/2009 | Owen | G06T 15/08 382/128 |
| 7,778,953 | B2 * | 8/2010 | Fujiwara | G06F 17/2775 382/176 |
| 8,370,293 | B2 * | 2/2013 | Iwase | G06F 16/51 707/608 |
| 8,620,689 | B2 * | 12/2013 | Krishnan | G16H 30/20 600/300 |
| 8,868,490 | B2 * | 10/2014 | Iwase | G06Q 10/06 707/608 |
| 8,918,739 | B2 * | 12/2014 | Butin | G06F 3/04855 715/825 |
| 9,251,508 | B2 * | 2/2016 | Bishop | G06Q 10/107 |
| 9,535,651 | B2 * | 1/2017 | Khalatian | G06F 3/1462 |
| 9,703,462 | B2 * | 7/2017 | Butin | G06F 9/451 |
| 9,922,026 | B2 * | 3/2018 | Sevenster | G06F 40/10 |
| 10,114,926 | B2 * | 10/2018 | Iwase | G16H 15/00 |
| 10,395,420 | B2 * | 8/2019 | Vilsmeier | G06T 15/503 |
| 10,402,483 | B2 * | 9/2019 | Fan | G06F 40/143 |
| 10,769,427 | B1 * | 9/2020 | Gajera | G06K 9/6262 |
| 10,838,699 | B2 * | 11/2020 | Dayanandan | G06F 8/10 |
| 10,936,351 | B2 * | 3/2021 | Voicu | G06F 9/451 |
| 10,942,713 | B2 * | 3/2021 | Kochura | G06F 8/38 |
| 10,990,876 | B1 * | 4/2021 | Neagovici | G06F 17/18 |
| 11,003,331 | B2 * | 5/2021 | Huang | G06F 3/0482 |
| 2005/0065423 | A1 * | 3/2005 | Owen | G16Z 99/00 600/407 |
| 2005/0065424 | A1 * | 3/2005 | Shah | G06T 15/08 600/407 |
| 2005/0190981 | A1 * | 9/2005 | Fan | H04N 19/90 382/243 |
| 2006/0231108 | A1 | 10/2006 | Novatzky et al. | |
| 2007/0192354 | A1 | 8/2007 | Wei et al. | |
| 2007/0286360 | A1 | 12/2007 | Chu et al. | |
| 2008/0058611 | A1 | 3/2008 | Tsubura | |
| 2008/0086700 | A1 * | 4/2008 | Rodriguez | H04M 1/27475 715/804 |
| 2008/0097762 | A1 | 4/2008 | Kunz et al. | |
| 2008/0195958 | A1 * | 8/2008 | Detiege | G06K 9/00449 715/765 |
| 2008/0201636 | A1 * | 8/2008 | Fujiwara | G06F 17/2775 715/700 |
| 2009/0031207 | A1 | 1/2009 | Molemaar | |
| 2009/0313495 | A1 | 12/2009 | Krishnan et al. | |
| 2010/0049740 | A1 * | 2/2010 | Iwase | G06F 19/00 705/7.27 |
| 2010/0131873 | A1 * | 5/2010 | Mejia | G16H 15/00 715/764 |
| 2011/0047488 | A1 * | 2/2011 | Butin | G06F 3/04842 715/762 |
| 2011/0154219 | A1 * | 6/2011 | Khalatian | G06F 3/1462 715/751 |
| 2012/0151380 | A1 * | 6/2012 | Bishop | G06Q 10/107 715/752 |
| 2012/0198362 | A1 * | 8/2012 | Urban | G06K 9/00476 715/762 |
| 2013/0024208 | A1 * | 1/2013 | Vining | A61B 8/5223 705/3 |
| 2013/0054613 | A1 * | 2/2013 | Bishop | G06F 17/30011 707/748 |
| 2013/0124459 | A1 * | 5/2013 | Iwase | G16H 30/40 707/608 |
| 2014/0075301 | A1 * | 3/2014 | Mihara | G06F 17/24 715/255 |
| 2014/0298449 | A1 * | 10/2014 | Low | G06F 3/01 726/19 |
| 2014/0316770 | A1 * | 10/2014 | Sevenster | G16H 15/00 704/9 |
| 2015/0006203 | A1 * | 1/2015 | Iwase | G06Q 10/06 705/3 |
| 2015/0089363 | A1 * | 3/2015 | Butin | G06F 3/04855 715/704 |
| 2016/0103792 | A1 * | 4/2016 | Bishop | G06Q 10/107 715/209 |
| 2016/0217114 | A1 * | 7/2016 | Fan | G06F 40/166 |
| 2018/0157386 | A1 * | 6/2018 | Su | G06F 9/451 |
| 2018/0203674 | A1 * | 7/2018 | Dayanandan | G06F 9/451 |
| 2019/0051400 | A1 * | 2/2019 | Iwase | G16H 30/20 |
| 2020/0012481 | A1 * | 1/2020 | Kochura | G06F 9/451 |
| 2020/0042148 | A1 * | 2/2020 | Huang | G06F 3/0484 |
| 2021/0019157 | A1 * | 1/2021 | Voicu | G06F 9/45512 |
| 2021/0103798 | A1 * | 4/2021 | Neagovici | G06F 17/15 |

OTHER PUBLICATIONS

Cheng, P., Informatics, Quality, Safety, and Policy; 2011; American Journal of Roentgenology; 196(5)A14-A17.

Florea, F., et al.; Automatic Image Annotation Combining the Content and the Context of Medical Images; 2007; IEEE Trans. on Int'l. Conference on Signals, Circuits and Systems; vol. 1; pp. 1-4.

HEALTHCAREGUY; Why vendors don't implement CCOW in legacy systems, The Healthcare IT Guy-Digital Health Nexus; 2006; http://www.healthcareguy.com/2006/02/23 accessed Sep. 24, 2015.

Health Level Seven, Inc.; HL7 Context Management "CCOW" Standard: Best Practices and Common Mistakes; Version 1.0; 2006. www.hl7.org/special/committees/visual/docs.cfm downloaded Sep. 24, 2015.

* cited by examiner

IMAGE VISUALIZATION OF MEDICAL IMAGING STUDIES BETWEEN SEPARATE AND DISTINCT COMPUTING SYSTEM USING A TEMPLATE

CROSS REFERENCE TO RELATED APPLICATIONS

This application is a national filing of PCT application Serial No. PCT/IB2014/060940, filed Apr. 23, 2014, published as WO 2014/174461 A2 on Oct. 30, 2014, which claims the benefit of U.S. provisional application Ser. No. 61/815,341 filed Apr. 24, 2013, which is incorporated herein by reference.

The following generally relates to viewing images such as computed tomography (CT) images, X-ray images, magnetic resonance (MR) images, positron emission tomography (PET) images, single photon emission computer tomography (SPECT) images, and/or other images.

Images generated in electronic format by systems such as CT, X-ray, MR, PET, SPECT, and/or other imaging systems have been viewed through visualization software executing on a computing system such as a computer. For example, such images have been viewed via a PACS (Picture Archiving and Communication System) and/or the like. Such systems have been provided by different vendors with basic common viewing capabilities, allowing for similar viewing across systems. Where a particular vendor includes advanced visualization tools with their software and/or customized information in the images, such tools and/or information may not be available and/or accessible via application software of another vendor.

An approach to mitigating such unavailability and/or inaccessibility of the advanced visualization tools and/or customized information is for the vendor to provide an add-on application or the like to the other vendors to run on the other vendors' systems. However, this requires running two different applications from two different vendors in the same software environment without sharing any information. As such, the user has to select and load the imaging data twice, one for each application/system, and possibly go back and forth between applications to view and/or manipulate the imaging data, rendering image viewing and/or manipulation tedious and consuming clinician time.

The CCOW (Clinical Context Object Workgroup) context sharing standard provides a limited solution to the above. With respect to Health informatics, the CCOW standard is an HL7 standard protocol that allows vendor independent disparate applications to synchronize in real time, at the user-interface level, and present information at the desktop and/or portal level in a unified manner. This standard requires that both vendors' applications adhere to the same standard. Unfortunately, the CCOW standard has not been implemented by majority of the vendors. In addition, this will likely not change in the future, partially due to conflicting business goals between vendors.

Aspects described herein address the above-referenced problems and others.

The following describes a system and/or method that facilitates sharing image viewing context between vendor visualization applications without integration of different software application from different vendors packages, neither by software integration, nor by compliance with a standard. However, the partial or full integration of the different software applications from the different vendors is also contemplated herein.

In one aspect, a visualization computing system includes a processor that executes computer readable instructions that capture a visual context of an imaging study displayed via a basic visualization application running on a vendor computing system, identify the study based on the captured visual context, load the study on the visualization computing system, and launch an advanced visualization application, which allows viewing and manipulation of the loaded study using advanced visualization tools unavailable by the basic visualization application.

In another aspect, a method includes capturing a screen layout of a study loaded in connection with a basic visualization application executing on a first computing system, identifying, based on the captured screen layout, an identification of the loaded study, and loading the identified study in connection with an advanced visualization application, which includes visualization tools in addition to those of the basic visualization, of a second different computing system.

In another aspect, a computer readable storage medium is encoded with one or more computer executable instructions, which, when executed by a processor of a computing system, causes the processor to: determine an identification of a study loaded in a basic visualization application executing on a first computing system based on a screen capture of the loaded study and a layout template of the basic visualization application, and load the identified study in connection with an advanced visualization application, which includes visualization tools in addition to those of the basic visualization, of a second different computing system.

The invention may take form in various components and arrangements of components, and in various steps and arrangements of steps. The drawings are only for purposes of illustrating the preferred embodiments and are not to be construed as limiting the invention.

FIG. 1 schematically illustrates an example visualization computing system that includes an advanced visualization application(s) and a context identifier.

Figure 1:
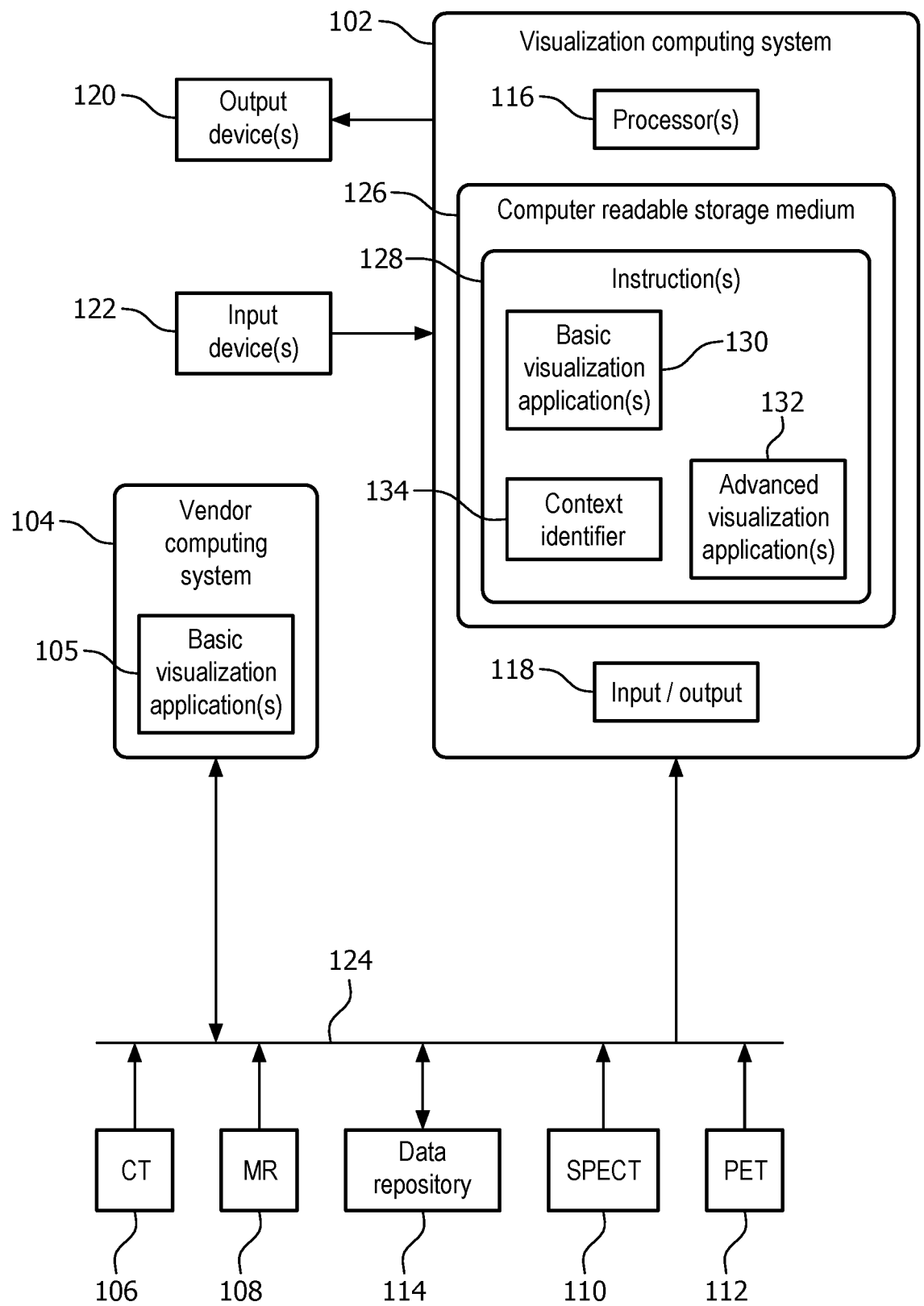

Initially referring to FIG. 1, a visualization computing system 102 is schematically illustrated in connection with a vendor computing system 104, imaging systems 106, 108, 110 and 112, and a data repository 114. In this example, the vendor computing system 104 includes basic visualization tools whereas the visualization computing system 102 includes the basic visualization tools and additional visualization tools such as vendor custom tools.

The visualization computing system 102 includes a processor(s) 116 such as a microprocessor, a central processing unit, a controller, or the like. The visualization computing system 102 further includes input/output (I/O) 118 that facilitates communication with an output device(s) 120 such as a display monitor, filmer, etc., with an input device(s) 122 such as a mouse, keyboard, etc., with a network 124, etc.

The visualization computing system 102 further includes a computer readable storage medium 126, which includes physical memory or other non-transitory memory. The processor(s) 116 executes computer readable instructions 128 encoded or embedded in the computer readable storage medium 126. The processor(s) 116 can also execute computer readable instructions carried by a signal, carrier wave, and other transitory (non-computer readable storage) medium.

In the illustrated example, the instructions 128 include a basic visualization application(s) 130, which, for this example, include instructions for basic viewing capabilities likely to be common across most vendor computing systems. The illustrated vendor computing system 104 also includes the basic visualization application(s)130, as well as a processor(s), computer readable storage medium, I/O, input and output devices, which are not shown for sake of clarity and brevity.

The instructions 128 further include an advanced visualization application(s) 132, which, for this example, include additional instructions for image viewing and/or manipulating capabilities that are not common to the vendor computing system 104 and/or part of the basic visualization application(s) 130. The instructions 128 further include a context identifier 134. As described in greater detail below, the context identifier 134 identifies a visualization context (or screen layout) of the vendor computing system 104, and employs this context with the visualization computing system 102 to present the same study in connection with the advanced visualization application(s) 132.

In one instance, this allows a user to seamlessly move from the vendor computing system 104 to the visualization computing system 102 when the user desires to use advanced visualization tools that are not available via the vendor computing system 104. Seamlessly means that the same study and the same image presented by the vendor computing system 104 is automatically identified, loaded and presented by the visualization computing system 102. In one instance, this mitigates having to integrate visualization applications of different vendors and/or comply with a standard screen layout utilized by multiple different vendors.

The illustrated visualization computing system 102 and/or the vendor computing system 104 obtain imaging data from one or more of the imaging systems 106, 108, 110 and 112, the data repository 114, and/or other device and/or storage. The imaging systems include a CT imaging system 106, an MR imaging system 108, a SPECT imaging system 110, and a PET imaging system 112. Other imaging systems are also contemplated herein. The data repository 114 may include one or more of a radiology information system (RIS), a hospital information system (HIS), an electronic medical record (EMR), a sever, a database, and/or the like.

The visualization computing system 102 can be activated to determine the visualization context of the vendor computing system 104 in response to a user activating the visualization computing system 102 to do so, for example, when the user determines they want to use the advanced visualization application(s) 132. In another instance, the visualization computing system 102 determines the context when the basic visualization application is employed and stores the context information and/or pre-loads the study on the visualization computing system 102.

The vendor computing system 104 and/or the visualization computing system 102 can be PACS and/or other computing systems.

Figure 2:
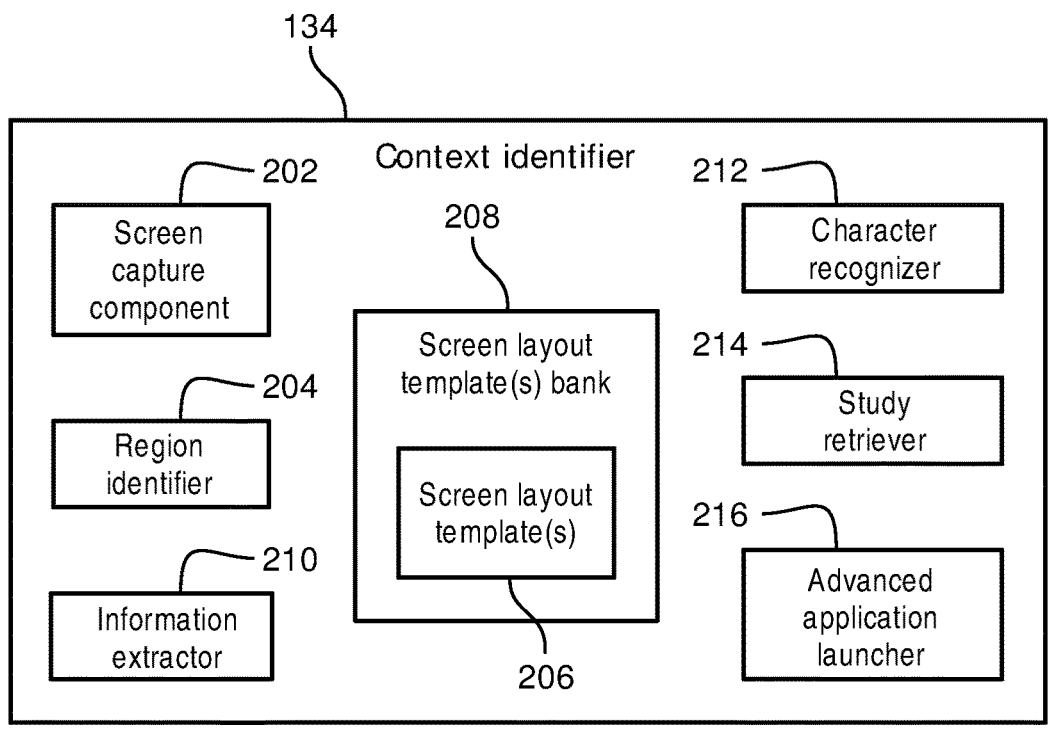
FIG. 2 illustrates an example of the context identifier.

Turning to FIG. 2, an example of the context identifier 134 is illustrated.

Figure 3:
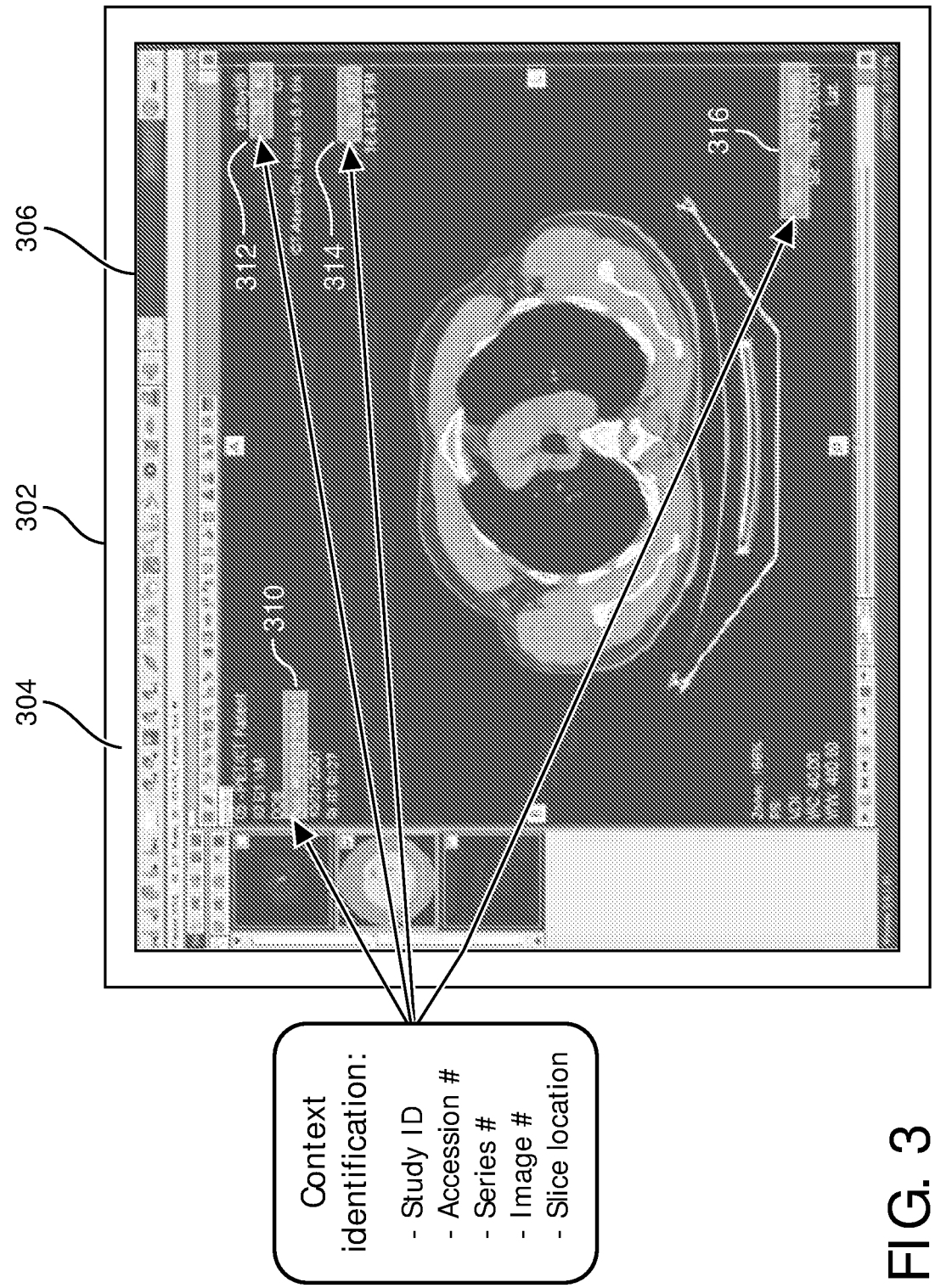
FIG. 3 illustrates an example of data displayed in a GUI for a basic visualization application running on a vendor computing system.

A screen capture component 202 captures the current context or content displayed, in a display monitor or the like, by the vendor computing system 104. An example of such content is depicted in FIG. 3 which shows a monitor 302 with a display region 304 in which a basic visualization graphical user interface (GUI) 306 corresponding to the basic visualization application 105 is displayed. In FIG. 3, a study has already been loaded and is visually presented in the GUI 306. The loaded data includes an image of a two dimensional axial slice of a scanned object and various information corresponding to the patient, the scan, the axil slice, etc. In this example, the screen capture component 202 visually captures the GUI 306.

Figure 4:
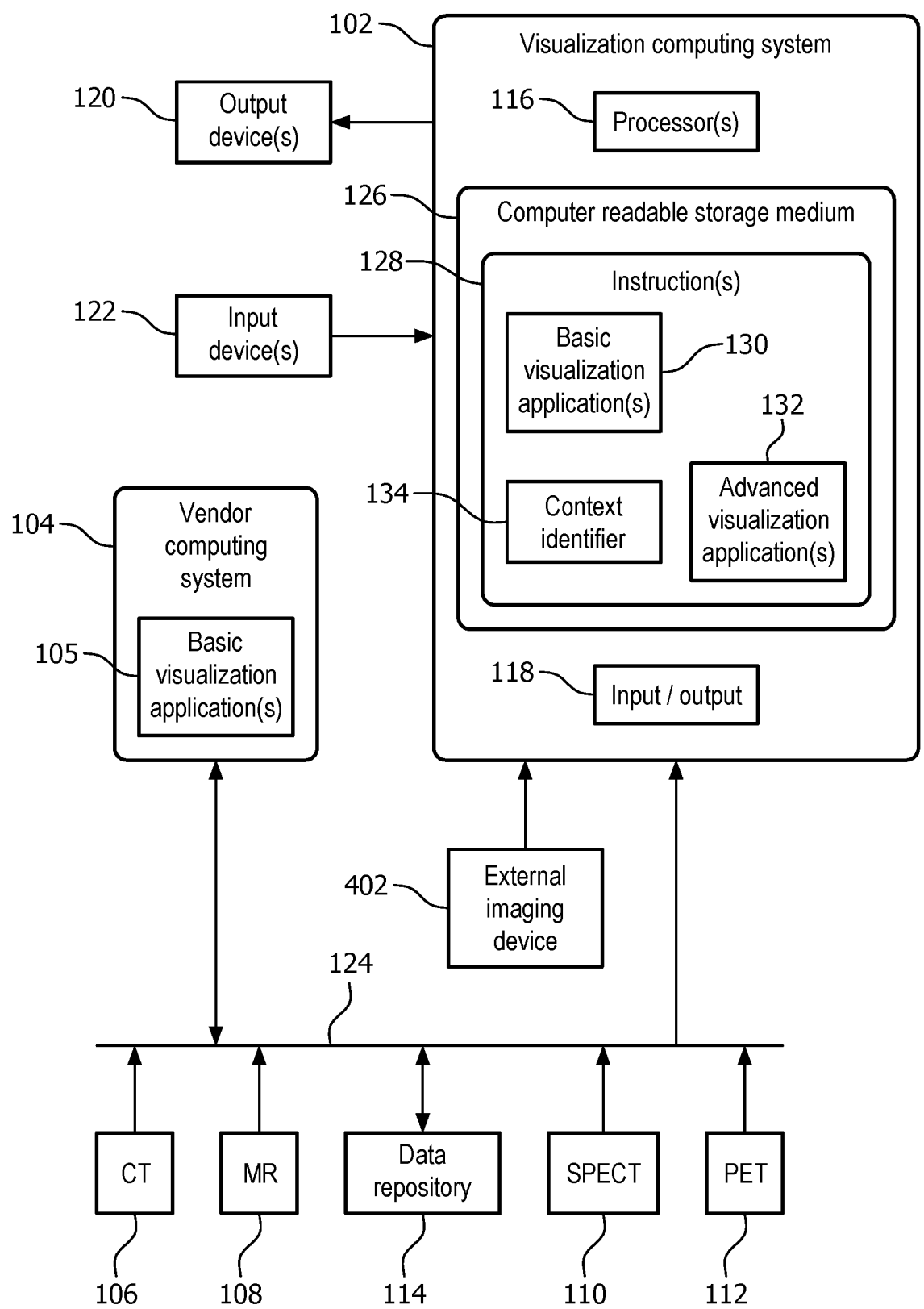
FIG. 4 illustrates an example of the visualization computing system in connection with an external imaging device.

In one instance, the screen capture component 202 includes a software module that is conveyed to and executed by the vendor computing system 104. The executing software module captures the screen in an electronic data format and conveys the electronic data to the visualization computing system 102. In another instance, the software module is otherwise conveyed to and executed by the vendor computing system 104, for example, over the network 124 via a server, from portable memory (e.g., CD/DVD, etc.), etc. In yet another instance, the screen capture component 202 is employed in connection with an external imaging device such as an optical sensor, such as a camera, a video recorder, or the like. This is shown in FIG. 4, which includes an external imaging device 402. In this case, the picture or video of the GUI 306 is sent to the visualization computing system 102.

Returning to FIG. 2, a region identifier 204 employs a pre-determined screen layout template(s) 206 from a template bank 208 to identify one or more regions in the captured screen shot. The particular template(s) 206 corresponds to the layout of information in the captured screen shot and can be identified, for example, from a plurality of different templates 206, based on a name and/or unique identification of the vendor of the vendor computing system 104, a name of the basic visualization software the vendor computing system 104, a user selected template, an identification of a viewing facility at which the images are being viewed, and/or other information. Turning briefly to FIG. 3, in this example, the template 206 identifies regions 310, 312, 314 and 316, e.g., by screen coordinates or otherwise. The template 206 also identifies what information is displayed in each of the one or more regions.

Returning to FIG. 2, an information extractor 210 extracts the information from the identified one or more regions of the captured screen shot. For example, in the example in FIG. 3, the template 206 identifies the region 310 as displaying a string and/or value corresponding to a unique identification of the study ("Study ID"), the region 412 as displaying a string and/or value corresponding to a series number ("Series #"), the region 314 as displaying a string and/or value corresponding to an image slice number ("Image #"), and the region 316 as displaying a string and/or value corresponding to a slice location ("Slice location"). The information extractor 210 extracts this information such that it extracts the "Study ID", the "Series #", the "Image #", and the "Slice location".

A character recognizer 212 interprets the extracted information to determine the meaning of the extracted information. For example, in FIG. 3, the character recognizer 212 interprets the extracted information corresponding to the "Series #" 312 as "#2", the "image #" as "#107", etc. A study retriever 214 retrieves the study, e.g., based on the interpreted extracted information corresponding to the unique identification of the study. The study can be retrieved from the CT imaging system 106, the MR imaging system 108, the SPECT imaging system 110, the PET imaging system 112 and/or other imaging system, the data repository 114, and/or other device.

An advanced application launcher 216 launches an advanced visualization application(s) 132. The particular application launched can be identified based on the interpreted extracted information. For example, where the interpreted extracted information includes information indicating the particular scan protocol, for example, a cardiac scan, the advanced application launcher 216 can select an advanced cardiac application from the advanced visualization application(s) 132 (FIG. 1). In another example, a user selects an advanced visualization application(s) 132 of interest, for example, via a GUI selection from a menu of available advanced applications. The menu may be presented in either or both of the vendor computing system 104 or the visualization computing system 102. In yet another example, a default advanced application is selected. The default application can be identified via a default file.

Figure 5:
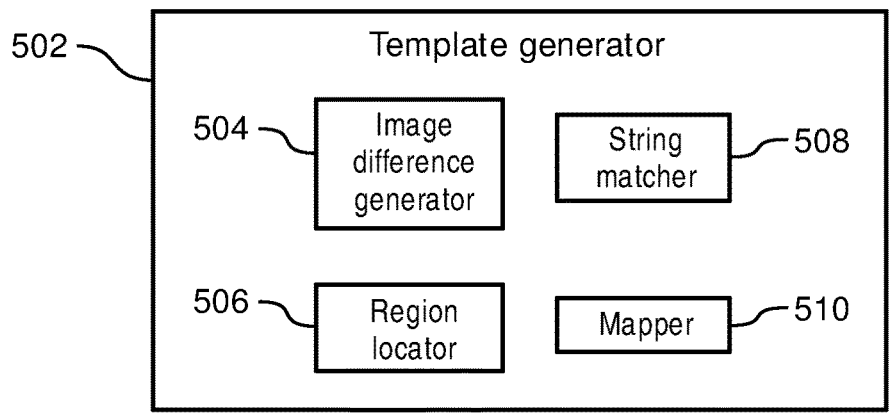
FIG. 5 illustrates an example screen layout template generator.

FIG. 5 illustrates an example template generator 502 that generates at least one of the templates 206.

The template generator 502 obtains (e.g., retrieves, receives, etc.) at least two screen shots of images of the same object (e.g., a calibration phantom) but with different but known textual information such as different "Study ID," "Series #," "Image #," "Slice location," and/or other displayed information. The screen shots can be obtained via the screen capture component 202 and/or otherwise. This may include loading two studies and capturing the screen layouts and/or receiving the screen layouts.

Figures 8, 9, 10:
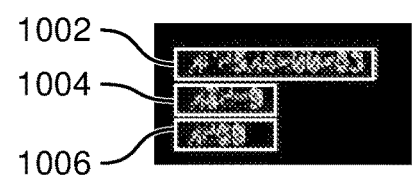
FIG. 8 illustrates textual information for a first screen shot with first textual information and an image of an object
FIG. 9 illustrates textual information for a second screen shot with second textual information, which is different from the first textual information, and the image of the object.
FIG. 10 illustrates a difference image generated by subtracting the screen layouts of FIGS. 8 and 9.

An image difference generator 504 subtracts the at least two screen shots, generating a difference image. Since the object is the same in the at least two screen shots, the object therein cancels out. However, the information in the textual information is different and thus the difference image will include regions with difference information. This is shown in FIGS. 8, 9 and 10. FIG. 8 shows textual information for a first screen shot, FIG. 9 shows different textual information for a second screen shot, and FIG. 10 shows the difference between the textual information in FIGS. 8 and 9.

A region locator 506 records coordinates to these regions. In this example, three regions are located, a first region 1002 corresponding to examination identification, a second region 1004 corresponding to series identification, and a third region 1006 corresponding to image identification. In this example, the three regions are adjacent to each other. In other instances, the regions may be located in different regions of the images, for example, as shown in FIG. 3 in connection with 310, 312, 314 and 316. In other examples, more or less regions are identified.

A string matcher 508 matches the known meaning of the textual information in the original at least two images using the coordinate information to locate the textual information. For example, in connection with FIG. 10, the string matcher 508 matches the location corresponding with 1002 with the string corresponding to the examination identification, the location corresponding with 1004 with the string corresponding to the series identification, and the location corresponding with 1006 with the string corresponding to the image identification.

A mapper 510 maps the identified strings to corresponding locations, generating a screen layout template identifying the regions of interest in the screen layout that includes textual information of interest. The above can be repeated for a plurality of different vendors such that a screen layout template is generated for the screen layout of each one of the plurality of different vendors. In another instance, a vendor provides the screen layout template for their screen layout. The templates can be stored in the visualization computing system 102 (as shown) or external thereto, for example, at a server.

Figure 6:
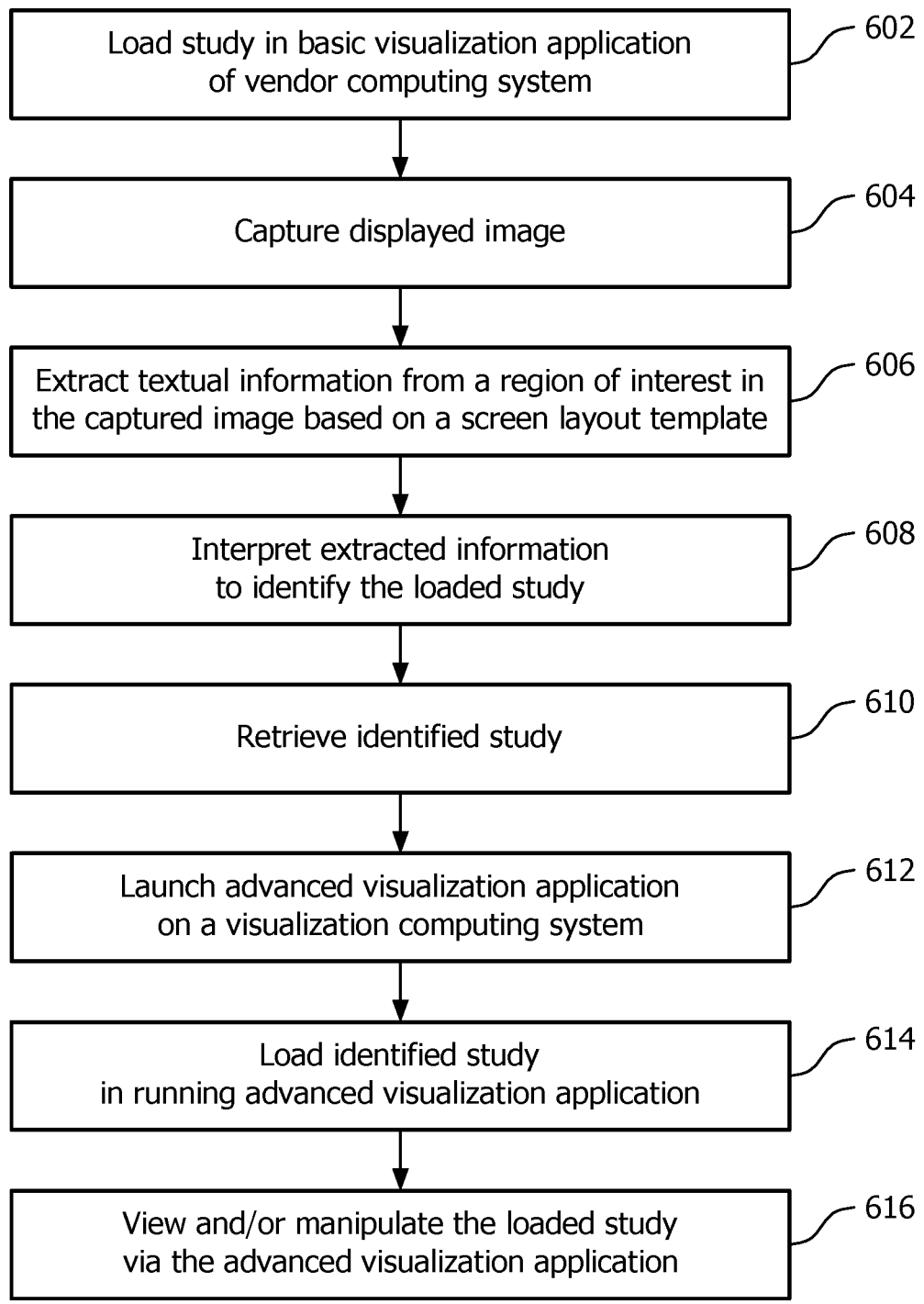
FIG. 6 illustrates an example method for identifying and using a visualization context of a vendor computing system with a visualization computing system with advanced visualization tools.
Figure 7:
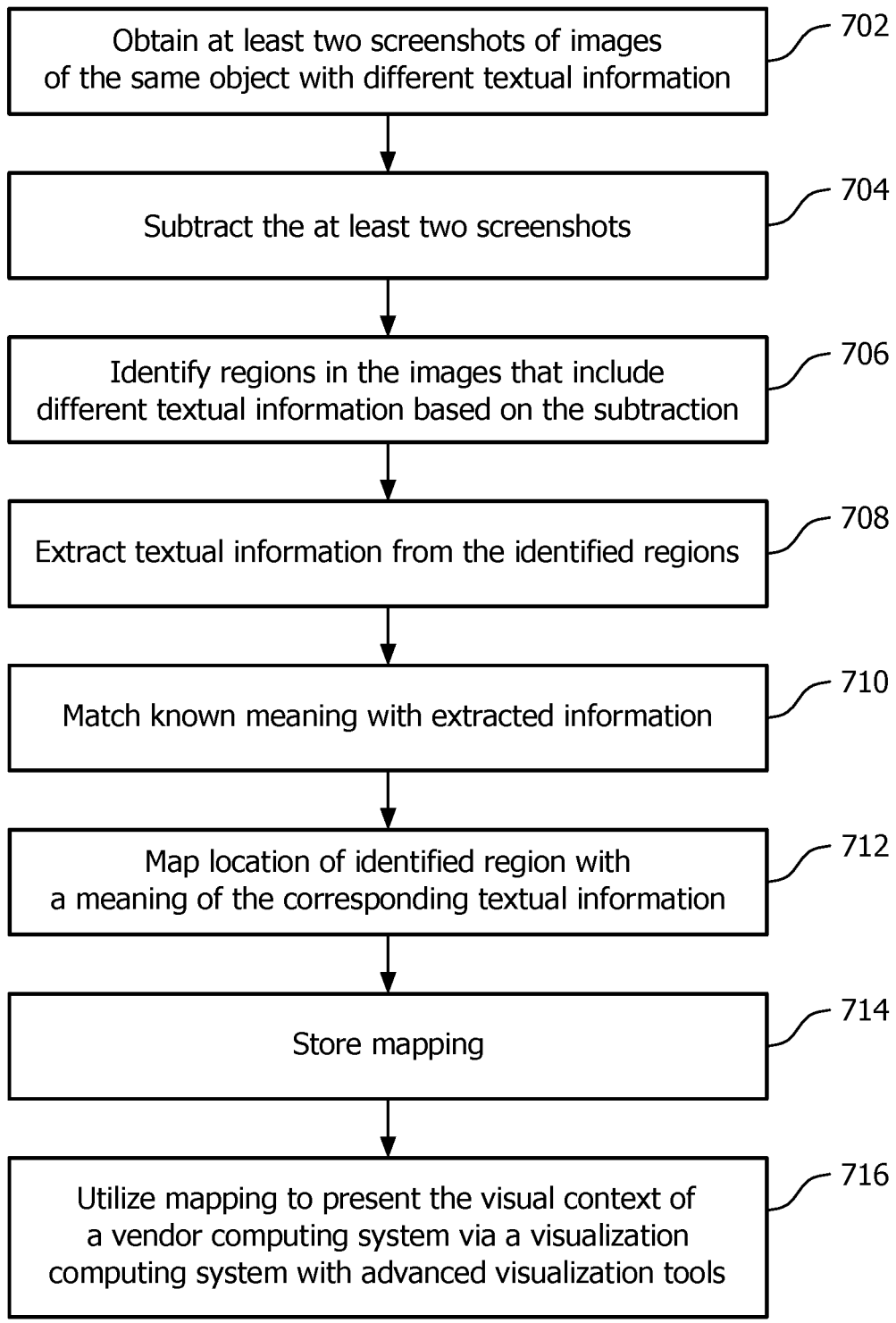
FIG. 7 illustrates an example method for generating screen layout templates.

FIGS. 6 and 7 illustrate methods in accordance with the description herein.

It is to be appreciated that the ordering of the acts in the methods is not limiting. As such, other orderings are contemplated herein. In addition, one or more acts may be omitted and/or one or more additional acts may be included.

FIG. 6 illustrate an example method for employing the visualization computing system 102.

At 602, a study is loaded into a basic visualization application executing on a vendor computing system.

At 604, an image displayed by the vendor computing system is captured.

At 606, textual information in regions of interest identified from a template is extracted from the captured image.

At 608, the extracted textual information in is interpreted to identify the study loaded in the basic visualization application.

At 610, the identified study is retrieved.

At 612, an advanced visualization application is launched on a visualization computing system, which is different from the vendor computing system.

At 614, the identified study is loaded in the advanced visualization application.

At 616, an operator of the visualization computing system view and/or manipulates the loaded study via the advanced visualization application.

FIG. 7 illustrate an example method for generating templates.

At 702, at least two screen shots of images of the same object but with different but known textual information are obtained for a basic visualization application running on a vendor computing system. This can be achieved by loading the studies side by side and performing a screen capture or by receiving already capture screen layouts.

At 704, the at least two screen shots are subtracted, generating a difference image.

At 706, regions of the difference image with the different known textual information are identified. Generally, regions in the at least two images with the same information will cancel out such that the only regions in the difference image with textual information are those regions that include different textual information.

At 708, the textual information in the identified regions is extracted.

At 710, the extracted textual information is matched with the known meaning.

At 712, the meaning of extracted textual information and the corresponding location is mapped, generating a screen layout template for the screen layout of the basic visualization application running on the vendor computing system.

At 714, the mapping is stored.

At 716, the mapping is utilized by the visualization computing system 102 to present a study loaded in the basic visualization application running on the vendor computing system via an advanced visualization application running on the visualization computing system 102 in the same visual context as it is presented in the basic visualization application running on the vendor computing system.

The above methods may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

In a variation, context identification is performed through the use of accessibility application programming interfaces (APIs) of an operating system of Microsoft, Apple, etc. Accessibility APIs allow an external application to introspect the user interface of another application in a non-intrusive fashion. These APIs are meant to enable accessibility tools such as screen readers to work with any application.

Furthermore, a screen context recognition (SCR) profile could be created based on a user interface (UI) hierarchical structure of the application and then used to retrieve the information from various UI elements. Profile creation can follow a very similar technique to the one above where images with known data are displayed. It is then possible to "search" the UI and look for the known markers to identify their matching UI elements.

The SCR system would need to be deployed on the target environment (PC) and can be very lightweight. It would have to include a resident agent that runs to capture and extract the context continuously.

To further ease the integration of dedicated applications that make use of the context information (which is often complex on PACS workstations), the SCR system could communicate context captures and changes to a server. This server would then be used by either a thin-client application such as the IntelliSpace Portal client or a web-based zero-footprint application which can then react to context changes appropriately.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A visualization computing system for visualizing images with a plurality of systems, comprising:
a processor that executes computer readable instructions that:
generates a screen layout template by:
obtaining a first screen shot and a second screen shot of a same object, wherein the first screen shot and the second screen shot include different textual information;
creating a difference image by subtracting common information from the first screen shot and the second screen shot such that the difference image includes difference information between the first screen shot and the second screen shot;
determining at least one region of different textual information in the first screen shot and the second screen shot that corresponds to a location of remaining information in the difference image and includes the different textual information;
matching the different textual information in the at least one region of different textual information to a known meaning, wherein the known meaning includes identifying information; and
mapping the matched different textual information to a corresponding location in the screen layout template;
captures a visual context of an imaging study of a patient displayed via a basic visualization application running on a first computing system, the basic visualization application including at least image viewing capabilities;
identifies the imaging study of the patient based on the captured visual context by employing a character recognition algorithm that interprets the extracted textual information, wherein the identified imaging study of the patient further comprises a series number, an image slice number, and a slice location,
wherein the imaging study is identified from displayed information within at least one region of textual information of interest in the captured visual context,
wherein the at least one region of textual information of interest corresponds to the location of the matched different textual information in the screen layout template;
loads the identified imaging study on the visualization computing system; and
launches, on the visualization computing system, (i) a visualization application that includes the basic visualization application and (ii) additional instructions for image viewing and manipulating capabilities that are unavailable to the first computing system, the additional instructions including a context identifier of the visualization computing system;
wherein the loaded study is transferred from the first computing system to the visualization computing system when the visualization tools in addition to those of the basic visualization application are selected by a user of the first computing system.

2. The visualization computing system of claim 1, wherein the template identifies the at least one region of textual information of interest that comprise textual information identifying the study in the captured visual context via screen coordinates.

3. The visualization computing system of claim 1, wherein the executing computer readable instructions further extract textual information from the at least one region of textual information of interest identified in the captured visual context.

4. The visualization computing system of claim 1, wherein the executing computer readable instructions identify the visualization application based on the interpreted extracted textual information that identifies an imaging study protocol that indicates a type of scan of the imaging study of the patient based on the captured visual context and launches the visualization application that corresponds to a same type of scan of the patient, wherein the imaging study of the patient is generated from at least one system selected from a group comprising of a computed tomography (CT) system, a magnetic resonance (MR) system, a single proton emission computed tomography (SPECT) system, and a positron emission tomography (PET) system.

5. The visualization computing system of claim 1, wherein the executing computer readable instructions map the different textual information to a type of data at and generate the template which comprises the one or more locations and the mapped type of data.

6. The visualization computing system of claim 1, wherein the first computing system and the visualization computing system are separate and distinct computing systems.

7. The visualization computing system of claim 1, wherein the captured visual context of the imaging study of the patient displayed via the basic visualization application running on the first computing system includes an image presented by the first computing system, and the processor executes said computer readable instructions that further:
identifies the slice location, a series number, and the image slice number based on the captured visual context;
wherein the launching of the visualization application includes presenting the same image presented by the first computing system in the launched visualization application.

8. A method for visualizing images with a plurality of systems, comprising:
with the first computing system, capturing a screen layout of an imaging study of a patient loaded in connection with a basic visualization application running on the first computing system, the basic visualization application including at least image viewing capabilities;
with a first computing system, identifying from the captured screen layout, extracted information including at least an identification of the loaded study comprising a series number, an image slice number, and a slice location and a type of scan within at least one region of textual information of interest;
with a second computing system, based on the extracted information, loading the identified study in connection with a visualization application corresponding to the type of scan, the visualization application including visualization tools in addition to those of the basic visualization application, the visualization tools including a context identifier of the second computing system, the visualization tools not being available to the first computing system;
wherein the loaded study is transferred from the first computing system to the second computing system when the visualization tools in addition to those of the basic visualization application are selected by a user of the first computing system.

9. The method of claim 8, wherein the template identifies the at least one region of textual information of interest in the captured visual context that identifies the imaging study of the patient.

10. The method of claim 9, further comprising:
extracting the textual information from the captured visual context according to templated identified location;
interpreting the extracted textual information; and
identifying a study protocol that indicates the type of scan based on the captured visual context.

11. The method of claim 10, further comprising:
launching the visualization application, which corresponds to a same type of scan, wherein the imaging study of the patient is generated from at least one system selected from a group comprising of a computed tomography (CT) system, a magnetic resonance (MR) system, a single proton emission computed tomography (SPECT) system, and a positron emission tomography (PET) system.

12. The method of claim 8, further comprising:
mapping the different textual information to a known type of data, and
generating the template which comprises the mapped type of data.

13. The method of claim 8, wherein the first computing system and the second computing system are separate and distinct computing systems.

14. The method of claim 8 further comprising:
generating a screen layout template by obtaining a first screen shot and a second screen shot of a same object, wherein the first screen shot and the second screen shot include different textual information, creating a difference image by subtracting common information from the first screen shot and the second screen shot, determining at least one region of different textual information in the first screen shot and the second screen shot that corresponds to a location of remaining information in the difference image and includes the different textual information, matching the different textual information in the in the at least one region of different textual information to a known meaning, wherein the known meaning includes identifying information, and mapping the matched different textual information to a corresponding location in the screen layout template;
wherein the at least one region of textual information of interest corresponds to the location of the matched different textual information in a screen layout template.

15. The method of claim 8 wherein:
the captured screen layout of the imaging study of the patient loaded in connection with the basic visualization application executing on the first computing system includes an image presented by the first computing system; and
the loading the identified study based on the extracted information includes presenting the same image presented by the first computing system in connection with the visualization application corresponding to the type of scan.

16. A system, wherein the system comprises a visualization computing system, comprising: a processor that executes computer readable instructions that
capture a screen contents of a first computing system, wherein the first computing system and the visualization computing system are separate and distinct computing systems, and wherein the first computing system displays an image of an imaging study via a graphical user interface of a basic visualization application, wherein the image is a CT image, an X-ray image, an MR image, a PET image, or a SPECT image, wherein the screen contents include a series number, an image slice number, and a slice location of the image,
determine information uniquely identifying the imaging study based on the captured screen contents,
load the imaging study on the visualization computing system, and
launch an advanced visualization application on the visualization computing system, wherein the advanced visualization application allows viewing and manipulation of the loaded imaging study using visualization tools unavailable by the basic visualization application,
wherein the visualization computing system is configured to capture the screen contents of the first computing system by retrieving electronic data representing the screen contents from a software module that is executed by the first computing system and that determines the electronic data by using an accessibility API to introspect the user interface of the basic visualization application;

the visualization computing system includes multiple advanced visualization applications; the executing computer readable instructions extract information indicating a particular scan protocol based on the captured screen contents, and select the advanced visualization application to be launched among the multiple advanced visualization applications based on the information indicating the particular scan protocol, wherein the system further comprises the first computing system, wherein the first computing system comprises the software module configured to determine the electronic data representing the screen contents by using the accessibility API to introspect the user interface of the basic visualization application, and to send the electronic data to the visualization computing system;

wherein the loaded study is transferred from the first computing system to the visualization computing system when the visualization tools in addition to those of the basic visualization application are selected by a user of the first computing system.

* * * * *